(12) United States Patent
Liu et al.

(10) Patent No.: US 8,703,208 B2
(45) Date of Patent: Apr. 22, 2014

(54) NANOMETER MESOPOROUS SILICA-BASED XEROGEL STYPTIC PROCESS AND ITS PREPARING PROCESS AND APPLICATION

(75) Inventors: Changsheng Liu, Shanghai (CN); Yuan Yuan, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 858 days.

(21) Appl. No.: 12/403,904

(22) Filed: Mar. 13, 2009

(65) Prior Publication Data

US 2009/0232902 A1   Sep. 17, 2009

Related U.S. Application Data

(63) Continuation-in-part of application No. PCT/CN2006/002907, filed on Oct. 30, 2006.

(30) Foreign Application Priority Data

Sep. 14, 2006   (CN) .......................... 2006 1 0116061

(51) Int. Cl.
*A61K 33/42* (2006.01)
*A61P 7/04* (2006.01)
*A61L 15/42* (2006.01)
*C01B 37/00* (2006.01)

(52) U.S. Cl.
USPC ........... 424/601; 424/422; 424/602; 424/600; 424/682; 514/184; 514/2

(58) Field of Classification Search
USPC .......... 424/601, 422, 602, 600, 682; 514/184, 514/2
See application file for complete search history.

(56) References Cited

U.S. PATENT DOCUMENTS

| | | | |
|---|---|---|---|
| 4,631,193 A | * | 12/1986 | Sobus .................. 426/330.4 |
| 4,822,439 A | | 4/1989 | Gauchel et al. |

(Continued)

FOREIGN PATENT DOCUMENTS

| | | |
|---|---|---|
| CN | 1535731 A | 10/2004 |
| CN | 1554607 A | 12/2004 |

(Continued)

OTHER PUBLICATIONS

Arthur T. Hubbard: Encylopedia of Surface and Colloid Science, vol. 4, 2002, Marcel Dekker, Inc., Basel, Switzerland.*

(Continued)

*Primary Examiner* — Ernst Arnold
*Assistant Examiner* — Hong Yu
(74) *Attorney, Agent, or Firm* — Hamre, Schumann, Mueller & Larson, P.C.

(57) ABSTRACT

The invention disclosed a novel mesoporous silica-based xerogel and its use in hemorrhage control. The mesoporous silica-based xerogel material has tunable mesopores (1-50 nm), high specific surface area (100-1400 m$^2$/g), macroscopical morphology (powder, film, disc, column, etc.) and adjustable compositions (SiO$_2$, CaO and P$_2$O$_5$, etc.) as well as good biodegradation. The mesoporous silica-based xerogels herein effectively promote the blood clotting under various conditions including slow and severe hemorrhage, even at the blood oozing site of bone defect. Meanwhile, the networks of silica-based xerogel with good elastic and mechanic properties, formed by adsorbing a large amount of water, can modulate the cell behavior and tissue growth, and thus promote the wound healing. Additionally, due to the mesoporous structure, the materials have the potential to load drug, thrombin and bioactive factors, which is favorable for the therapeutical efficacy.

21 Claims, 5 Drawing Sheets

(56) References Cited

U.S. PATENT DOCUMENTS

| | | | |
|---|---|---|---|
| 5,643,447 A | * | 7/1997 | Lev et al. .................. 210/198.3 |
| 2004/0120971 A1 | * | 6/2004 | Koskinen et al. .......... 424/204.1 |

FOREIGN PATENT DOCUMENTS

| CN | 1727011 A | 2/2006 |
|---|---|---|
| WO | WO 2006/035098 A2 | 4/2006 |

OTHER PUBLICATIONS

Kumar et al., "MCM-41, MCM-48 and related mesoporous adsorbents: their synthesis and characterization", Colloids and Surfaces A: Physicochemical and Engineering Aspects 187-199, 2001, 109-116.*

International Search Report of PCT/CN2006/002907, dated Jun. 21, 2007.

Dickneite et al. "A comparison of fibrin sealants in relation to their in vitro and in vivo properties." Thrombosis Research, vol. 112, 2003, pp. 73-82.

Marx et al. "Characterizing fibrin glue performance as modulated by heparin, aprotinin, and factor XIII." J Lab Clin Med, vol. 140(3), 2002, pp. 152-160.

Vaiman et al. "Effectiveness of second-generation fibrin glue in endonasal operations." Otolaryngology-Head Neck Surgery, vol. 126(4), 2002, pp. 388-391.

Ryšavá et al. "Surface interactions of oxidized cellulose with fibrin(ogen) and blood platelets." Sensors and Actuators B, 90, 2003, pp. 243-249.

Christenson et al. "Oxidized Regenerated Cellulose Gauze for Hemostasis of a Two-Stage Interpolation Flap Pedicle." Dermatol Surg, vol. 30(12) part. 2, Dec. 2004, pp. 1593-1594.

Alam et al. "Application of a Zeolite Hemostatic Agent Achieves 100% Survival in a Lethal Model of Complex Groin Injury in Swine." The Journal of Trauma: Injury, Infection and Critical Care, vol. 56(5), May 2004, pp. 974-983.

Ahuja et al. "Testing of Modified Zeolite Hemostatic Dressings in a Large Animal Model of Lethal Groin Injury." The Journal of Trauma: Injury, Infection and Critical Care, vol. 61(6), Dec. 2006, pp. 1312-1320.

* cited by examiner

NANOMETER MESOPOROUS SILICA-BASED XEROGEL STYPTIC PROCESS AND ITS PREPARING PROCESS AND APPLICATION

FIELD OF THE INVENTION

The invention relates to a biomedical material and its preparation and use. Specifically, the invention relates to a novel mesoporous silica-based xerogel useful as a hemostatic material and its preparation and use.

BACKGROUND OF THE INVENTION

Uncontrolled hemorrhage contributes the main cause of syndrome after injuries in many circumstances, which is a threat to human life. Meanwhile, rapid and effective hemostasis is an important part of clinical surgery and first aid in the filed. According to a crude investigation, approximately 500 tons of hemostats are used in clinical every year in China. Therefore, an effective hemostatic material for prompt hemorrhage-arresting and wound healing in hospital and in field is eagerly needed all over the world.

Up to the present, traditional hemostatic materials include first-aid kits, tourniquets, bandages and the sterilized dressings that can be used to compensate the first-aid kit in a hemostatic treatment. However, these hemostatic materials have been found to have the shortcomings such as being less effective in combined injuries, multiple injuries and wounds with a large injury area, and not so ready-to-use as desired for a first aid in field.

In order to overcome these shortcomings, a series of novel hemostatic materials have been developed and used in clinical applications in recent years. Based on the main components, these new hemostatic materials can be classified into Fibrin Glues (FG), Oxidized Celluloses (OC), Oxidized regenerated celluloses (ORC) and mineral zeolite-based hemostats. The Fibrin Glues exhibit effective hemostatic property, good adhesion and good biocompatibility. The accepted hemostatic mechanism with these materials is to mimic the spontaneous coagulation process, while being independent of platelets and coagulation factors, which makes them especially effective in halting bleeding in organs suffering coagulation dysfunction. Since Tisseel/TiSSUCOI fibrin glues (manufactured by Immuno AG Co., Austria) being approved by FDA in 1998, more of these materials have been rapidly developed. To date, the commercially available fibrin-based glue products include Beriplast P, Hemaseel, Biocol, Boheal and Quixil, etc. As for the oxidized cellulose and oxidized regenerated cellulose, these materials have good degradable, antibacterial and hemostatic properties, and are especially effective to arrest slow bleeding. At present, the examples of commercially available OC and ORC hemostats include the Oxycel series and the Surgicel series. The hemostatic mechanism with these materials is proposed to be that the acidic carboxyl group in the molecule binds with the $Fe^{3+}$ ion in the hemoglobin to generate the acidic $Fe^{3+}$-hemin in blood, whereby red-brown gel blocks are formed to close the end of capillaries, and then to arrest the bleeding. Inert mineral zeolite particles were first found to have a good hemostatic effect by Francis X. Hursey in 1980s, and was patented as U.S. Pat. No. 4,822,349 in 1989. In 2002, Z-Medica Corporation produced a type of new hemostatic materials under the named of QuikClot™. These materials have been approved by FDA and commercially available. It has been shown that these zeolite-based materials are superior to other hemostatic materials in both hemostatic efficacy and survival rate. The hemostatic mechanism of these mineral zeolites mainly resides in their extraordinary selective adsorption of water relative to erythrocyte, platelet and other coagulation factors, which leads to a quick hemostasis by concentrating the clotting factors at the injury site. As a further improvement, CN1727011A designed and developed a mesoporous zeolite hemostatic agent. Due to the unique mesoporous structure and tunable pore size, the mesoporous zeolite could stop bleeding more efficiently and more quickly. And, the new agent could further improve therapeutic effects by adsorbing antibiotics or analgesics on the material. In view of these, mesoporous molecular sieves have a broader market prospects than the traditional zeolite hemostats.

Although these new hemostatic agents, to some extent, have overcome some shortcomings of the traditional hemostatic materials, and are useful in certain clinical applications, they still have some significant drawbacks. For instance, Fibrin Glues have been blamed of a high production cost, the risk of causing blood-borne diseases and infections in human beings and animals, the complicated procedure of application, being slow in arresting bleeding and less effective in arresting bleeding of large blood vessels. The oxidized cellulose and oxidized regenerated celluloses have been reported to incline to adsorb blood and then expand, which may cause neurothlipsis. For mineral zeolite hemostats, they may generate residues in the tissue as "foreign bodies", because they are not biodegradable. And, the mineral zeolite hemostats become exothermal on adsorbing moisture, which may burn the tissue when being used in a massive bleeding wound.

SUMMARY OF THE INVENTION

An object of the present invention is to overcome the problems in the prior arts by providing a mesoporous silica-based xerogel useful as a hemostatic material and its preparation and use.

The present invention is largely based on the following facts. The zeolite-based hemostats' hemostasis effects can be attributed to their excellent adsorption capability based on the high porosity and the selective adsorption of moisture. Mesoporous molecule sieves, being characteristic of the mesoporous structure and the tunable pore size, can provide an extraordinarily quick and efficient hemostasis effect. Silica-based xerogels are a type of new bio-materials advantageously featuring both biodegradability and bioactivity. Then, the Mesoporous Silica-based xerogels of the present invention, possessing the advantages from both the mesoporous molecule sieves and the silica-based xerogels, can not only provide a quick and efficient hemostatic effect but also a desirable biodegradability, while being devoid of the problems in the prior arts. Further, the material of the invention can also release beneficial ions such as Si to modulate the cellular events and to facilitate the wound healing.

In the $1^{st}$ aspect of the invention, it is provided a biomesoporous silica-based xerogel useful as a hemostatic material, comprising silicon oxide, calcium oxide and phosphor oxide at a molar ratio of about 50-100:0-25:0-25.

In a preferred embodiment, the mesoporous silica-based xerogel is biodegradable.

In a preferred embodiment, the mesoporous silica-based xerogel has an in vivo exothermic effect lower than that of zeolite.

In a preferred embodiment, when in vivo exothermic effect of the mesoporous silica-based xerogel is the measured in the method as shown in example 6, the maximum temperature in the wounds treated is <42° C., preferred <40, and more preferred <39.5° C.

In a preferred embodiment, the mesoporous silica-based xerogel is biocompatible.

In a preferred embodiment, the mesoporous silica-based xerogel has a pore size ranging from 1 nm to 50 nm.

In a preferred embodiment, the mesoporous silica-based xerogel has a specific surface area of 100-1400 m$^2$/g.

In a preferred embodiment, the mesoporous silica-based xerogel is in the form of powder, film, disc or column.

In a preferred embodiment, the silicon oxide, calcium oxide and phosphor oxide are at a molar ratio of 50-100:5-20:5-20.

In a preferred embodiment, the xerogel further comprises antibiotics or thrombin.

In the 2$^{nd}$ aspect of the invention, it is provided a method for preparing the mesoporous silica-based xerogel according to claim, wherein said method comprises the steps of:

dissolving a silica source precursor, a phosphorus source precursor and a calcium source precursor in an aqueous ethanol solution;

adjusting the pH of the obtained solution to the range of 2-8 using HCl, and stirring for 1-4 h to obtain a stable sol;

aging the obtained sol at 20-100° C. for 5-200 h, and then drying the sol; and calcinating the dried sol at 500-700° C. for 2-10 h to eliminate the solvent.

In a preferred embodiment, the silica source is selected from the group consisting of tetraethoxysilane (TEOS), tetramethoxysilane (TMOS), tetrabutoxysilane (TBOS), sodium silicate, potassium silicate and lithium silicate.

In a preferred embodiment, the calcium source is selected from the group consisting of $CaCl_2$, $Ca(NO_3)_2$, $(CH_3COO)_2Ca \cdot H_2O$, methoxy calcium, ethoxy calcium and methoxyethoxy calcium.

In a preferred embodiment, the phosphorus source is selected from the group consisting of TMP, TEP, $Na_3PO_4$, $Na_2HPO_4$, $NaH_2PO_4$, $K_3PO_4$, $K_2HPO_4$ and $KH_2PO_4$.

In a preferred embodiment, the silica source, the phosphorus source and calcium are provided at a molar ratio of 50-100:0-25:0-25.

In the 3$^{rd}$ aspect of the invention, it is provided a method of hemostatic treatment, comprising the step of applying the mesoporous silica-based xerogels according to claim 1 to a bleeding site of the subject in need of to stop bleeding.

In a preferred embodiment, the bleeding site includes slow and severe hemorrhage, inaccessible bleeding wounds, and blood oozing in bone defect.

DETAILED DESCRIPTION OF THE INVENTION

The invention provides a kind of mesoporous silica-based xerogel with the characteristics of tunable mesopores (1-50 nm), high specific surface area (100-1400 m$^2$/g), good biodegradation, as well as good skin regeneration. The invention further provides the application of the mesoporous silica-based xerogel in hemorrhage control.

The mesoporous silica-based xerogel of the present invention is mainly comprised of silicon oxide, calcium oxide and phosphor oxide at a molar ratio of about 50-100:0-25:0-25. The mesoporous silica-based xerogel has a pore size ranging from about 1-50 nm and a specific surface area of about 100-1400 m$^2$/g. The mesoporous silica-based xerogel material of the invention can be in any desirable forms such as powder, films, discs, columns, etc.

A typical procedure for preparing the mesoporous silica-based xerogel according to the present invention may include the following steps:

(1) Dissolving a silica source precursor, a phosphorus source precursor and a calcium source precursor in a 10-60% aqueous ethanol solution.

(2) Adjusting the pH of the obtained solution in the range of about 2-8, preferably about pH 4-6, by adding HCl in drops, and stirring for about 1-4 hrs to obtain a sols.

(3) Aging the obtained sol at about 20-100° C. for about 5-200 h, and, subsequently, drying the aged sol at about 20-180° C. for about 2-48 h. The step of drying can utilize any suitable methods known in the art, which include but are not limited to the normal temperature drying, the freeze-drying, the vacuum drying and the gradient heating, etc.

(4) Finally, the obtained gel is calcinated at about 500-700° C. for about 2-10 h to eliminate the solvent, whereby the product is obtained.

Suitable silica sources include but are not limited to, for example, TEOS, TMOS, TBOS, sodium silicate, potassium silicate and lithium silicate;

Suitable calcium sources include but are not limited to, for example, $CaCl_2$, $Ca(NO_3)_2$, $(CH_3COO)_2Ca \cdot H_2O$, methoxy calcium, ethoxy calcium, methoxyethoxy calcium, etc;

Suitable phosphorus sources include but are not limited to, for example, TMP, TEP, $Na_3PO_4$, $Na_2HPO_4$, $NaH_2PO_4$, $K_3PO_4$, $K_2HPO_4$ and $KH_2PO_4$, etc.

The molar ratio of silicon oxide:calcium oxide:phosphorus pentoxide is 50~100:0~25:0~25.

The mesoporous silica-based xerogel of the invention can be used for a variety of medical applications including the arrest of slow bleeding, the arrest of severe hemorrhage and hemostasis at a oozing site in bone defect, which is not readily accessible.

In one embodiment, the nanometer mesoporous silica-based xerogel styptic material of the invention was applied onto the ear of the rabbit to stop the bleeding of vein. The blood clotting time in the hemostasis without pressure or with pressure was measured and the same amount of Chinese medicine Yunnan Baiyao was used as control. The results showed that, without pressure, the treatment with the xerogel of the invention and the treatment with the Yunnan Baiyao had the same or similar clotting time, while with pressure, the former needed significantly less time to arrest the bleeding than the latter. The wound healing results of 1 week, 2 weeks and 1 month after applying showed that the xerogel of the invention had a much better performance in wound healing than the Yunnan Baiyao.

When applied, the xerogel of the invention may be evenly applied to the wounded area. The xerogel will rapidly adsorb the moisture and concentrate the coagulation factors at the site, form a barrier layer on the surface of wound and lead to a quick scaring and hemostasis. Further, on adsorbing a large amount of water, a network of silica-based xerogel will be formed, which is elastic and has desirable mechanic properties. The network modulates the cellular events and tissue generation, and thereby promotes the wound healing. Along with the tissue growth and wound healing, the material remained at the wound site is absorbed and biodegraded by the body. Additionally, the mesoporous structure can be advantageously utilized to load drugs and bioactive factors such as thrombin to improve the healing efficacy. In view of these, the mesoporous silica-based xerogel of the invention is predicted to bean ideal hemostatic material.

The invention is further illustrated by the following examples. It is appreciated that these examples are only intended to illustrate the invention, but not to limit the scope of the invention. For the experimental methods in the following examples, they are performed under routine conditions or as instructed by the manufacturers, unless otherwise specified.

Example 1

Figure 1:
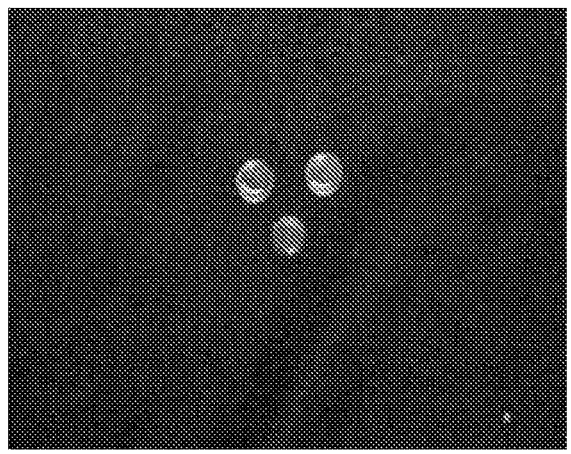
FIG. 1: Morphology of the mesoporous silica-based xerogel of the invention.
Figure 2:
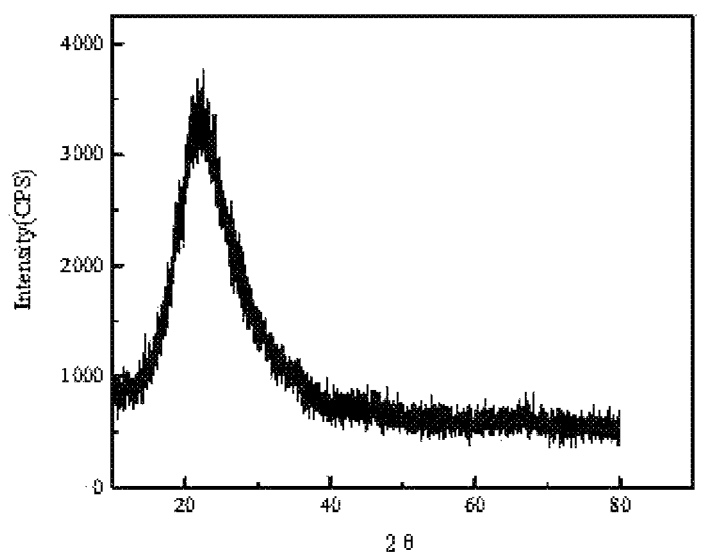
FIG. 2: XRD patterns of the mesoporous silica-based xerogel of the invention.
Figure 3:
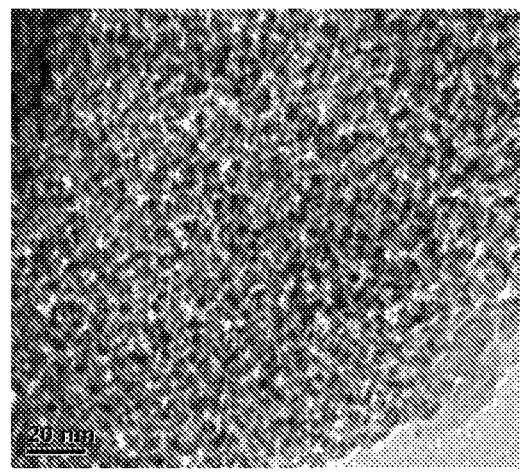
FIG. 3: TEM of the mesoporous silica-based xerogel of the invention.
Figure 4:
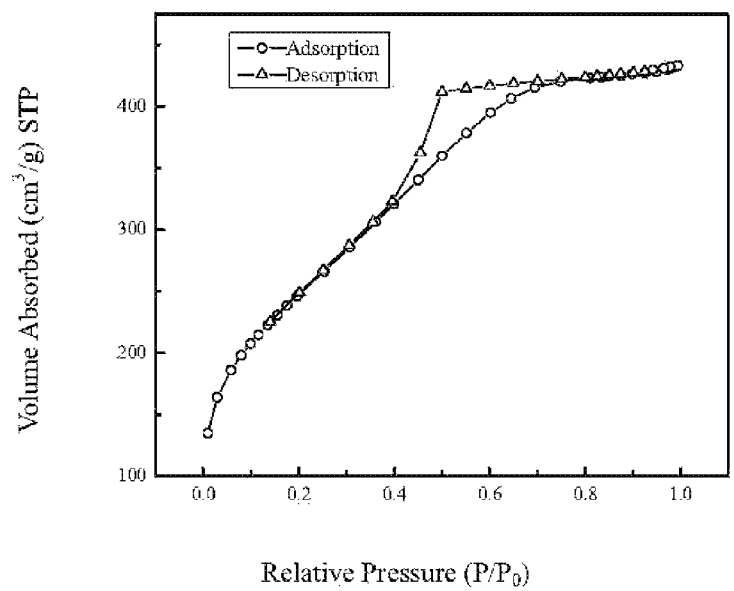
FIG. 4: $N_2$ adsorption-desorption isotherms of the mesoporous silica-based xerogel of the invention. 1—adsorption isotherm; 2—desorption isotherm.
Figure 5:
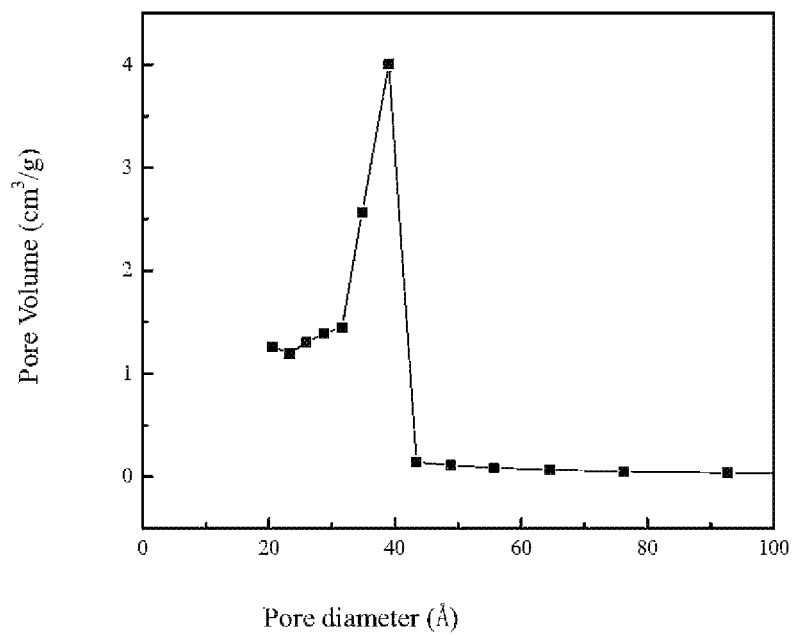
FIG. 5: Pore size distribution of the mesoporous silica-based xerogel of the invention.

10 g of TEOS was dissolved in a mixture of 5.4 g of deioned water and 2 g of ethanol with vigorous stirring for 10 min. The pH of the solution was adjusted to pH 3 using a 1N HCl solution, and the obtained solution was stirred for another 2 h. Thereafter, the obtained sol was poured and sealed into a polyethylene mold, and aged therein for 2 d. The aged product was then dried at 180° C. for 4 h. Microscopic examination showed that the as-synthesized xerogels were in the form of a smooth and transparent bulk (FIG. 1). The $N_2$ adsorption-desorption results showed that the obtained calcium-free silica-based xerogel had a pore size of 3 nm and a surface area of 670 $m^2/g$. The product was labeled as L-1.

Example 2

10 g of TEOS, 3.36 g of TMP and 2.67 of $CaCl_2$ were dissolved in a mixture of 8 g of deioned water and 8 g of ethanol with stirring for 10 min at the room temperature. The pH of the solution was adjusted to pH 3 by using a 1N HCl solution, and the solution was stirred for another 2 h. Then, the obtained sol was poured and sealed into a polyethylene mold, and was aged therein for 2 d. The molded gel was freeze-dried for 10 hrs. The dried product was calcinated in a corundum crucible at 700° C., and then cooled to the room temperature. The calcinated product was grinded and filtered through a 150 mesh filter. The obtained powder was a calcium-containing silica-based xerogel hemostat, and was stored before use. The crystallographic structure, the morphology, the pore size and the pore size distribution were measured by XRD, SEM and BET, respectively, and the results were shown in FIGS. 2, 3, 4 and 5. The results demonstrated that the obtained as-synthesized xerogel had the porous structure typical of amorphous silica. The $N_2$ adsorption-desorption results showed a type-IV isotherm, a type-H hysteresis loop, and an evident step in the range of relative pressure (Ps/P0) between 0.43 and 0.67. These were consistent with the characteristics of a two-dimensional hexagonal mesoporous structure, which indicated that the product had an ordered mesoporous structure. As measured, the product had a surface area of 850 $m^2/g$, a pore size of 3.8 nm and a narrow pore size distribution. The xerogel of this example was labeled as L-2.

Example 3

15 g of TEOS, 2.16 g of TMP and 1.71 of $CaCl_2$ were dissolved in a mixture of 8 g of deioned water and 8 g of ethanol with stirring for 10 min at the room temperature. The pH of the solution was adjusted to pH 6 by adding 1N HCl in drops, and the solution was stirred for another 2 h. Then the obtained sol was poured and sealed into a polyethylene mold, and was aged therein for 2 d. The molded gel was freeze-dried for 10 hrs. The dried product was calcinated in a corundum crucible at 700° C., and then cooled to the room temperature. The calcinated product was grinded and filtered through a 150 mesh filter. The obtained powder was a calcium-containing silica-based xerogel hemostat, and was stored before use. The $N_2$ adsorption-desorption results showed that the obtained silica based xerogel had a pore size of 50 nm and a surface area of 650 $m^2/g$. This product was labeled as L-3.

Example 4

10 g of TEOS, 3.36 g of TMP and 2.67 of $CaCl_2$ were dissolved in a mixture of 10 g of deioned water and 10 g of ethanol with stirring for 10 min at the room temperature. The pH of the solution was adjusted to pH 6 by using a 1N HCl solution. The solution was stirred for another 2 h. Then the obtained sol was poured and sealed into a polyethylene mold, and was aged therein for 2 d. The molded gel was freeze-dried for 10 h. The dried product was calcinated in a corundum crucible at 500° C., and then cooled to the room temperature. The calcinated product was grinded and filtered through a 150 mesh filter. The obtained powder was then stored before use. The product was a calcium-containing silica based xerogel hemostat with a pore size of 30 nm and a surface area of 1100 $m^2/g$. This product was labeled as L-4.

Example 5

Figure 6:
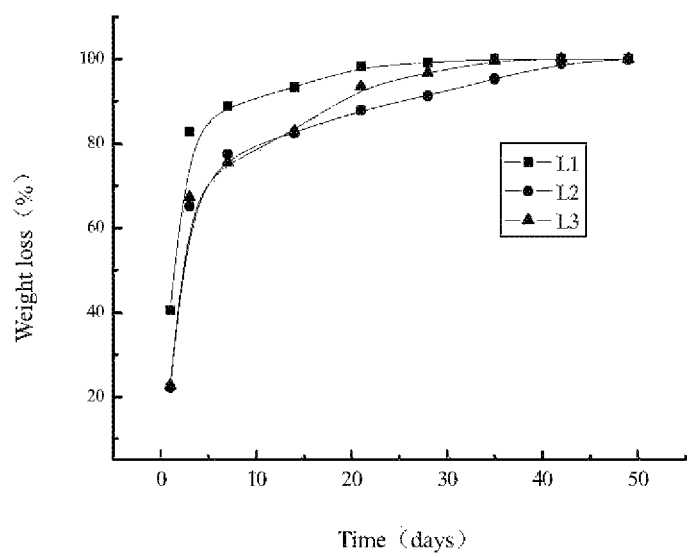
FIG. 6: The degradation performances of the mesoporous silica-based xerogel of the invention under different conditions.

The in vitro biodegradability of the silica based xerogels (labeled as L-1, L-2 and L-3) prepared in examples 1, 2 and 3 was investigated. The L-1, L-2 and L-3 samples were separately immerged in three sealed containers each containing 25 mL of SBF solution. The systems were incubated in a constant-temperature incubator at 37° C. At the time points of 1 d, 3 d, 7 d, 14 d, 21 d, 28 d, 35 d, 42 d and 49 d, samples were collected, filtered, washed with deioned water and dried at 100° C. for 2 h. The degradation rate was calculated from the weight loss. FIG. 6 showed that the degradation of the prepared materials were relatively fast in the first 7 days (a degradation of over 60%), and then slowed down until a complete degradation by day 40 or so. It can be seen then, the mesoporous silica based xerogels prepared according to the present invention had good biodegradability.

Example 6

The hemostatic performance of the silica based xerogel of the invention was evaluated in an animal model using the product of example 2 (labeled as L-2).

1) Method of Evaluation

The Measurement of Blood Clotting Time

Animal: New Zealand White Rabbit, male, 6-month old, 2.24 Kg weight, clean grade (provided by Animal Center of Fudan University School of Medicine).

Control: Yunnan Baiyao, which is a powdered hemostatic medicine and also one of the well known Traditional Chinese Medicines.

Method 1: Hemostasis Without Pressure: Bleeding was induced by punching the medial ear vein of the rabbit's left ear with the needle of a 5 mL plastic syringe. The blood was rapidly wiped off using a cotton ball, and the prepared xerogel or the Yunnan Baiyao was immediately applied onto the wounded area, at the same time, the stopwatch was started to measure the time needed for clotting.

The In Vivo Exothermic Effects:

To examine the in vivo exothermic effects, in all animals, the temperature variations were measured according to the proposed methods. In a typical assay, two mercury thermometers were placed in different sites of the interface between the agents and the incised muscles while the higher of the two readings was recorded. All the data were collected every 30 seconds till the end of the study period.

Method 2: Hemostasis With Pressure: Bleeding was induced by transecting the rabbit's ear vein at a ⅓ depth, and the wound was pressed using a cotton ball to prevent an uncontrolled bleeding without the pressure. Then, the contaminated cotton ball was replaced with a new one (100 mg in weight) which was coated with 100 mg of the xerogel or the Yunnan Baiyao. After pressing for about 1 min, the pressure was removed and the bleeding was examined. The pressure was reloaded if bleeding continued. The above was repeated until the bleeding is completely arrested. The bleeding time was recorded.

Wound Healing Experiment.

The rabbit was dehaired on the back using scissors and an electric razor. 3 mm deep and 5 mm wide incisions were created on the naked back in the pattern of "#". The two horizontal incisions were created as shallow and narrow. The left incision along the longitudinal axis was treated with the prepared xerogel, while the right one with the Yunnan Baiyao. The upper right independent short incision was also treated with the Yunnan Baiyao. The treated sites were pressed to ensure that the agents were fully in contact with the wounded area. The two horizontal incisions were left untreated and taken as the blank control. The wounds were not covered. The healing was monitored.

2) Results and Evaluation.

The Measurement of the Clotting Time

Figure 7:
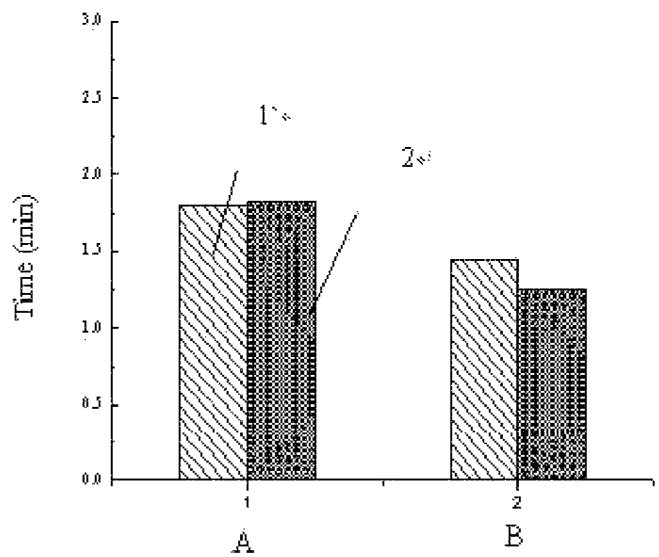
FIG. 7: Comparison of the clotting time between the mesoporous silica-based xerogel of the invention and the Yunnan Baiyao. 1—Yunnan Baiyao, 2—the mesoporous silica-based xerogel of the invention.

The results were shown in FIG. 7. 1—the Yunnan Baiyao, 2—the mesoporous silica-based xerogel of the invention A—without pressure, B—with pressure. FIG. 7 showed that, without pressure, the treatment with the xerogel of the invention and the treatment with the Yunnan Baiyao had no significant difference in clotting time, while with pressure, the former needed significantly less time to arrest the bleeding than the latter. This indicated that the mesoporous silica-based xerogel of the invention had a much better hemostatic efficacy.

The In Vivo Exothermic Effects

The exothermic effects examined by measuring the temperature indicated that the maximum temperature in the wounds treated by L-2 agent was 39.2° C., greatly lower than the temperature of over 50° C. associated with the mineral zeolite agent, measured with the same method. These results suggested that the L-2 agent exhibited very mild exothermic effects that were not harmful to the tissue around.

Wound Healing Experiment.

Figure 8:
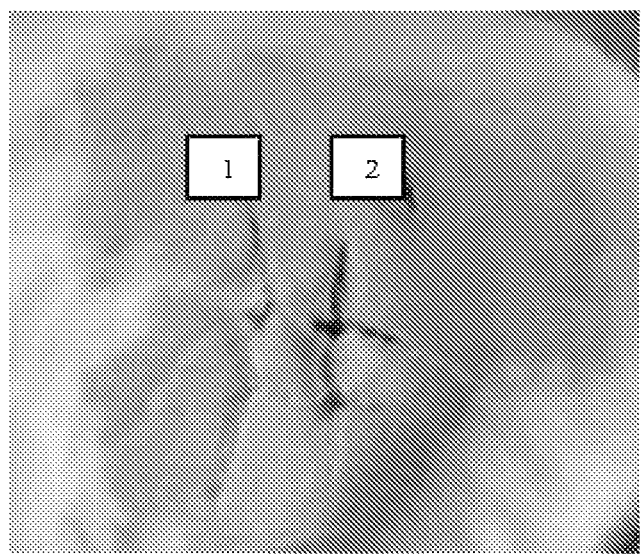
FIG. 8: Comparison of the wound healing between the mesoporous silica-based xerogel of the invention and the Yunnan Baiyao 1 week after the administration. 1—the mesoporous silica based xerogel; 2—the Yunnan Baiyao.
Figure 9:
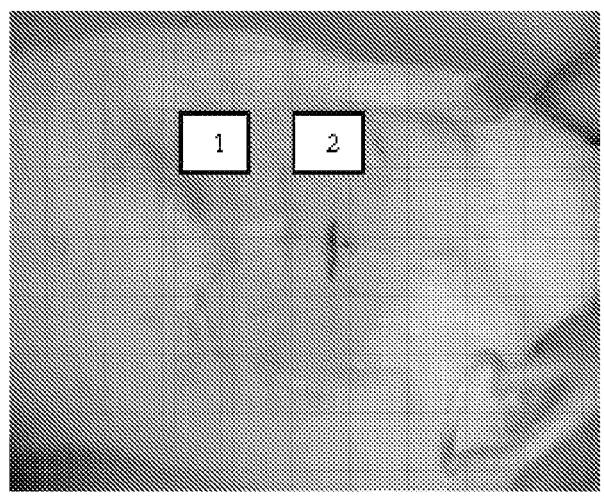
FIG. 9: Comparison of wound healing between the mesoporous silica-based xerogel of the invention and the Yunnan Baiyao 2 weeks after the administration. 1—the mesoporous silica-based xerogel; 2—the Yunnan Baiyao.
Figure 10:
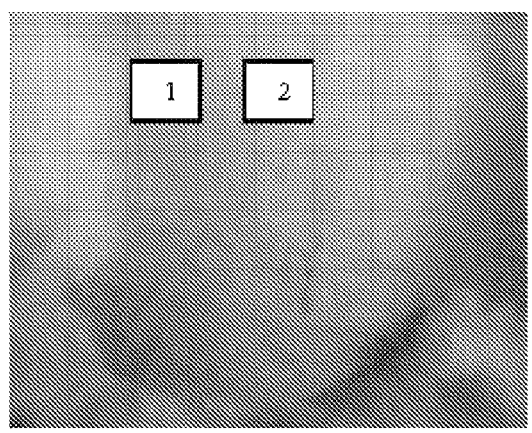
FIG. 10. Comparison of would healing between the mesoporous silica-based xerogel of the invention and the Yunnan Baiyao 1 month after the administration. 1—the mesoporous silica-based xerogel; 2—the Yunnan Baiyao.

The results of wound healing after the treatment with the xerogel of the invention and the Yunnan Baiyao for 1 week, 2 weeks and 1 month were shown in FIG. 8, FIG. 9 and FIG. 10, respectively. 1—the mesoporous silica based xerogel of the invention, 2—the Yunnan Baiyao.

The results showed that, in the first week, a yellowish scar formed at the left incision, and the wounded surface was flat and did not swell; The healing of the right incision was retarded, wherein a massive dark scars formed, and a severe swelling was observed around the wound.

2 weeks later, at the left incision, the scars shed off, the incision substantially closed up. New dermal tissues grew well, and the new skin lifted slightly above the around. At the right incision, the incision was desiccated and shrank. The scars did not shed off, and the wound did not heal up.

1 month later, the left incision completely healed up, and the skin at the wounded site was smooth and flat. The right incision as the control was obviously less well in condition.

It can be seen then, by significantly reducing swelling, minimizing scaring and proud flesh formation and shortening recovery time, the mesoporous silica-based xerogel of the invention has a much better performance in wound healing than the Yunnan Baiyao.

Example 7

10 g of TEOS, 3.36 g of TMP and 2.67 of $CaCl_2$ were dissolved in a mixture of 8 g deioned water and 8 g of ethanol with stirring for 10 min at the room temperature. The pH of the solution was adjusted to pH 6 using a 1N HCl solution, and the solution was stirred for another 2 h. 20 mL of 0.5% tobramycin aqueous solution was added into the obtained solution, and the mixture was stirred for 1 h. Then, the obtained sol was poured and sealed into a polyethylene mold, and aged therein for 2 d. The molded product was freeze-dried for 10 h and then stored before use. The obtained product was a calcium-containing silica based xerogel hemostat with a pore size of 30 nm and a surface area of 1100 $m^2/g$. The product was further tested in the animal experiments as above, and the results showed that the prepared tobramycin-containing mesoporous silica-based xerogel had a good hemostatic efficacy.

Example 8

5 g of TEOS, 1.68 g of TMP and 1.34 of $CaCl_2$ were dissolved in a mixture of 4 g deioned water and 4 g of ethanol with stirring for 10 min at the room temperature. The pH of the solution was adjusted to pH 4 by using a 1N HCl solution, and the solution was stirred for another 2 h. Then the obtained sol was poured and sealed into a polyethylene mold, and was aged therein for 2 d. The molded product was freeze-dried for 10 h. The dried product was calcinated in a corundum crucible at 700° C., and then cooled to the room temperature. The calcinated product was grinded and filtered through a 150 mesh filter. The prepared powder was immersed in 10 mL of 0.5% thrombin aqueous solution for 5 h, and then freeze-dried for 10 h. The product was further tested in the animal experiments as above, and the results showed that the prepared thrombin-containing mesoporous silica-based xerogel had a good hemostatic efficacy.

Example 9

In Vitro Biocompatibility

Method:

The cell viability of the prepared silica-based xerogels prepared in examples 1 and 2 (labeled as L-1 and L-2) was investigated by MTT assays using mouse myoblast cells line (ACTT, C2C12). The cell viability without silica-based xerogels was used as control.

Briefly, C2C12 cells were cultured in Dulbecco's Modified Eagle's Medium (DMEM) with 0.11 g/L L-glutamine, 2.2 g/L sodium bicarbonate, 10% fetal bovine serum and 2% antibiotics (200 ug/mL penicillin and 200 ug/mL streptomycin) for 8 days. Medium was changed twice a week. The cells from passages 5 through 15 were seeded into 96 well plates at a density of 5,000 cells per well and then were exposed to various amounts of L-1 and L-2 in the range of 0.078-1.25 mg/mL. After incubation in a fully humidified atmosphere of 5% $CO_2$ at 37° C. for 1 d, 2 d, 3 d and 4 d, the cell viabilities were assayed by MTT assays. The results were reported as means of at least five wells and presented as viability of cells compared with control (without silica-based xerogels).

Figure 11:
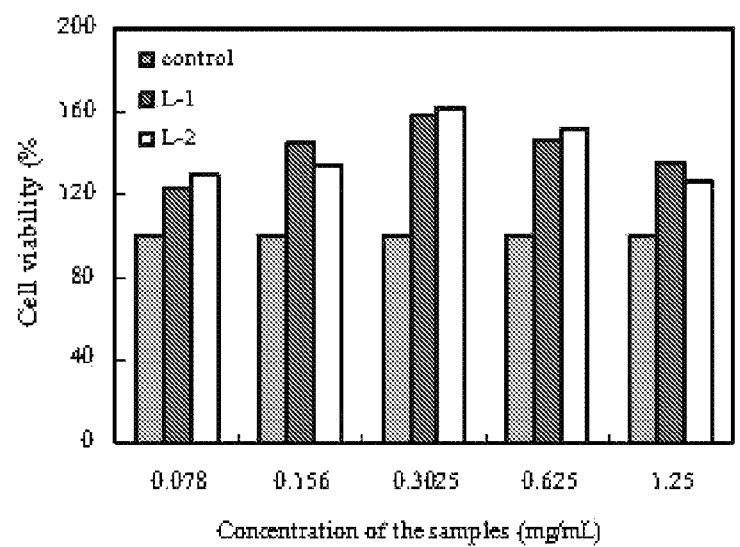
FIG. 11 shows that the mesoporous silica-based xerogels of the invention have good biocompatibility.

Results:

From the FIG. 11, it can be seen that compared with the control, the cell viability after exposure to L-1 and L-2 were all obviously increased at the concentration from 0.078 mg/mL to 1.25 mg/mL, indicating that the prepared mesoporous silica-based xerogels have good biocompatibility.

Example 10

In Vitro Hydration Heat

The in vitro hydration heat of the silica-based xerogels prepared in example 1 and example 2 (labeled as L-1 and L-2) was measured and compared with the traditional mineral zeolite.

The hydration heat was measured using an adiabatic typed temperature calorimeter system composed of a calorimeter, a stirring apparatus, electric heater and a thermometer, etc. 225 mL deionized water and 4.5-4.8 g of L-1, L-2 or mineral zeolite were mixed under magnetic stirrer in the calorimeter. The increasing of the water temperature was measured. The heating of device and the record of dynamic curve were operated automatically by computer control.

Table 1 shows the temperature increasing induced by the water adsorption of xerogels and the ordinary zeolite. It can be seen that the ordinary zeolite introduced more than 4☐, while the silica-based xerogel could only cause little temperature increasing, 1.1☐ for L-1 and 1.4☐ for L-2, an obvious low heat generation.

TABLE 1

Temperature changes of silica-based xerogels after water adsorption

| Samples | Temperature increased (☐) |
|---|---|
| Traditional zeolite | 4.6 |
| L-1 | 1.1 |
| L-2 | 1.4 |

All the documents cited herein are incorporated into the invention as reference, as if each of them is individually incorporated. Further, it would be appreciated that, in the above teaching of the invention, the skilled in the art could make certain changes or modifications to the invention, and these equivalents would still be within the scope of the invention defined by the appended claims of the present application.

What is claimed is:

1. A mesoporous silica-based xerogel useful as a hemostatic material, comprising silicon oxide, calcium oxide and phosphor oxide at a molar ratio of about 50-100:5-20:5-20, the mesoporous silica-based xerogel has a porous structure that is amorphous, wherein the xerogel is obtained by a method consisting of:
   dissolving a silica source precursor, a phosphorus source precursor and a calcium source precursor in an aqueous ethanol solution;
   adjusting the pH of the obtained solution to a range of 2-8 using HCl, and stirring for about 1 to about 4 hours to obtain a stable sol;
   aging the obtained sol at about 20 to about 100° C. for about 5 to about 200 hours, and then drying the sol; and
   calcinating the dried sol at about 500 to about 700° C. for about 2 to about 10 hours to eliminate the solvent.

2. The mesoporous silica-based xerogel of claim 1, wherein said mesoporous silica-based xerogel is biodegradable.

3. The mesoporous silica-based xerogel of claim 2, wherein said mesoporous silica-based xerogel has an in vivo exothermic effect lower than that of zeolite.

4. The mesoporous silica-based xerogel of claim 3, wherein when in vivo exothermic effect of the mesoporous silica-based xerogel is measured in the method as shown in example 6, the maximum temperature in the wounds treated is <42° C.

5. The mesoporous silica-based xerogel of claim 1, wherein said mesoporous silica-based xerogel is biocompatible.

6. The mesoporous silica-based xerogel of claim 2, wherein said mesoporous silica-based xerogel has a pore size ranging from 1 nm to 50 nm.

7. The mesoporous silica-based xerogel of claim 2, wherein said mesoporous silica-based xerogel has a specific surface area of 100-1400 $m^2/g$.

8. The mesoporous silica-based xerogel of claim 2, wherein said mesoporous silica-based xerogel is in the form of powder, film, disc or column.

9. The mesoporous silica-based xerogel of claim 2, wherein the xerogel further comprises antibiotics or thrombin.

10. A method for preparing the mesoporous silica-based xerogel according to claim 1, wherein said method consisting of: dissolving a silica source precursor, a phosphorus source precursor and a calcium source precursor in an aqueous ethanol solution; adjusting the pH of the obtained solution to a range of 2-8 using HCl, and stirring for about 1 to about 4 hours to obtain a stable sol; aging the obtained sol at about 20 to about 100° C. for about 5 to about 200 hours, and then drying the sol; and calcinating the dried sol at about 500 to about 700° C. for about 2 to about 10 hours to eliminate the solvent.

11. The method of claim 10, wherein the silica source is selected from the group consisting of tetraethoxysilane (TEOS), tetramethoxysilane (TMOS), tetrabutoxysilane (TBOS), sodium silicate, potassium silicate and lithium silicate.

12. The method of claim 10, wherein the calcium source is selected from the group consisting of $CaCl_2$, $Ca(NO_3)_2$, $(CH_3COO)_2Ca.H_2O$, methoxy calcium, ethoxy calcium and methoxyethoxy calcium.

13. The method of claim 10, wherein the phosphorus source is selected from the group consisting of trimethyl phosphate (TMP), triethyl phosphate (TEP), $Na_3PO_4$, $Na_2HPO_4$, $NaH_2PO_4$, $K_3PO_4$, $K_2HPO_4$ and $KH_2PO_4$.

14. The method of claim 10, wherein the silica source, the phosphorus source and calcium are provided at a molar ratio of 50-100:0-25:0-25.

15. A method of hemostatic treatment, comprising the step of applying the mesoporous silica-based xerogels according to claim 1 to a bleeding site of the subject in need of to stop bleeding.

16. The method of claim 15 wherein the bleeding site includes slow and severe hemorrhage, inaccessible bleeding wounds, and blood oozing in bone defect.

17. The mesoporous silica-based xerogel of claim 4, wherein the maximum temperature in the wounds treated is <40° C.

18. The mesoporous silica-based xerogel of claim 4, wherein the maximum temperature in the wounds treated is <39.5° C.

19. The mesoporous silica-based xerogel of claim 1, wherein the silica source is selected from the group consisting of tetraethoxysilane (TEOS), tetramethoxysilane (TMOS), tetrabutoxysilane (TBOS), sodium silicate, potassium silicate and lithium silicate.

20. The mesoporous silica-based xerogel of claim 1, wherein the calcium source is selected from the group consisting of $CaCl_2$, $Ca(NO_3)_2$, $(CH_3COO)_2Ca.H_2O$, methoxy calcium, ethoxy calcium and methoxyethoxy calcium.

21. The mesoporous silica-based xerogel of claim 1, wherein the phosphorus source is selected from the group consisting of trimethyl phosphate (TMP), triethyl phosphate (TEP), $Na_3PO_4$, $Na_2HPO_4$, $NaH_2PO_4$, $K_3PO_4$, $K_2HPO_4$ and $KH_2PO_4$.

* * * * *